(12) United States Patent
Gatti et al.

(10) Patent No.: US 8,269,022 B2
(45) Date of Patent: Sep. 18, 2012

(54) POLYMORPHS OF ENANTIOPURE ERDOSTEINE

(75) Inventors: Pier Andrea Gatti, San Genesio E Uniti (IT); Matteo Zacche', Vanzago (IT); Massimo Nicola, Pavia (IT)

(73) Assignee: Edmond Pharma S.R.L, Milan (IT)

( * ) Notice: Subject to any disclaimer, the term of this patent is extended or adjusted under 35 U.S.C. 154(b) by 268 days.

(21) Appl. No.: 12/742,679

(22) PCT Filed: Nov. 10, 2008

(86) PCT No.: PCT/EP2008/009499
§ 371 (c)(1),
(2), (4) Date: May 13, 2010

(87) PCT Pub. No.: WO2009/062659
PCT Pub. Date: May 22, 2009

(65) Prior Publication Data
US 2010/0249435 A1    Sep. 30, 2010

(30) Foreign Application Priority Data
Nov. 16, 2007 (EP) ..................................... 07022263

(51) Int. Cl.
*C07D 333/32* (2006.01)
(52) U.S. Cl. ........................................................ 549/63
(58) Field of Classification Search ...................... 549/63
See application file for complete search history.

(56) References Cited

FOREIGN PATENT DOCUMENTS
EP    0 061 386    9/1982
FR    2 502 153    9/1982

*Primary Examiner* — Taofiq A Solola
(74) *Attorney, Agent, or Firm* — Lucas & Mercanti, LLP

(57) ABSTRACT

The present invention provides novel crystalline polymorphs of enantiopure Erdosteine, referred to as Form I and Form II, and processes for the preparation thereof.

10 Claims, 10 Drawing Sheets

POLYMORPHS OF ENANTIOPURE ERDOSTEINE

This application is a U.S. national stage of PCT/EP2008/009499 filed on Nov. 10, 2008, which claims priority to and the benefit of European Application No. 07022263.3 filed on Nov. 16, 2007, the contents of which are incorporated herein by reference.

FIELD OF THE INVENTION

The present invention relates in general to Erdosteine, in particular to enantiopure Erdosteine in the form of crystalline polymorphs and to processes for the preparation thereof.

BACKGROUND OF THE INVENTION

Erdosteine, (chemical name 2-[N-3-(2-oxotetrahydrothienyl)]acetamido)-thioglycolic acid) of formula I was first disclosed in FR 2,502,153 and U.S. Pat. No. 4,411,909.

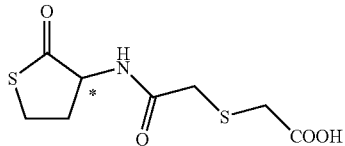

Formula 1

Racemic R,S-Erdosteine is used in the therapy of diseases of the respiratory tract thanks to its mucolytic properties. The racemate exists in a single solid-state form, whose physical characterization is reported in table 1 below.

TABLE 1

Characterization of Racemic Erdosteine

| X-ray powder diffraction pattern 2theta (deg) (FIG. VII) | Infrared absorption peaks (FIG. VIII) | DSC heating curve (FIG. IX) |
|---|---|---|
| 18.2 | 1796 cm$^{-1}$ | Melting peak in range 141-168° C. |
| 19.7 | 1740 cm$^{-1}$ | Onset at 156° C. |
| 20.1 | 1686 cm$^{-1}$ | Small shoulder at 155° C. |
| 21.5 | 1675 cm$^{-1}$ | |
| 25.9 | 1609 cm$^{-1}$ | |
| 27.4 | 1561 cm$^{-1}$ | |
| 28.4 | 1162 cm$^{-1}$ | |
| 31.3 | | |
| 32.8 | | |
| 36.7 | | |

A drawback associated to the use of racemic Erdosteine is its poor flowability and solubility, which negatively affects manufacturing processes of finished pharmaceutical forms and bioavailability. In fact, when a powder does not flow easily, glidants need to be added in order to prepare solid pharmaceutical forms such as tablets or capsules.

Other important properties of solid pharmaceutical forms are the solubility and the dissolution rate in aqueous fluids (in particular in gastric juices); these properties influence the dosage and the bioavailability of active principles.

In the pharmaceutical field, polymorphs of active principles often allow to improve the manufacturing process of finished pharmaceutical forms. Both flowability and solubility depend in fact on the solid state form of the active principle, which is in turn influenced by the conformation and orientation of the molecules in the unit crystalline cell. The unit cell defines a particular polymorph and may give rise to a specific thermal behaviour, X-ray crystallographic pattern and infrared absorption. Each polymorph may thus possess specific solid-state properties like flowability and dissolution rate.

Thus, it would be desirable to provide polymorphs of Erdosteine and processes for the preparation thereof, in order to overcome its poor flowability and solubility.

DESCRIPTION OF THE INVENTION

It has now been found that pure Erdosteine enantiomers, i.e. R-Erdosteine (formula 2 below) and S-Erdosteine (Formula 3 below) exhibit a polymorphic behaviour, each giving rise to two different polymorphs, herein after referred to as Form I and Form II (polymorph I and II), characterized by a specific thermal behaviour, X-ray diffraction pattern and infrared absorption.

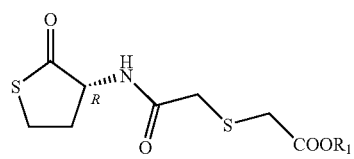

Formula 2

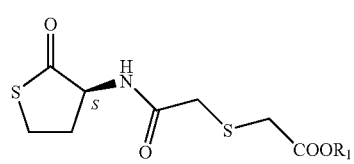

Formula 3

Thus, in one embodiment, the invention provides a crystalline polymorph of substantially enantiomerically pure Erdosteine, referred to as Form I, characterized by the following physical properties:

X-ray powder diffraction pattern with peaks at about 17.0, 20.1, 22.8, 23.4, 27.3, 28.0, 29.1, 30.6, 33.2±0.2 degrees two-theta, substantially as depicted in FIG. 1;

infrared absorption spectrum with peaks at about 1740, 1692, 1683, 1607 and 1576 cm-1, substantially as depicted in FIG. 2;

melting point at about 112-134° C. (onset at 123° C.), with a DSC thermogram substantially as depicted in FIG. 3. These data are reported in Table 2.

TABLE 2

Characterization of Erdosteine Form I

| X-ray powder diffraction pattern 2theta (deg) (FIG. 1) | Infrared absorption peaks (FIG. 2) | DSC heating curve (FIG. 3) |
|---|---|---|
| 17.0 | 1740 cm$^{-1}$ | Melting peak in range 112-134° C. |
| 20.1 | 1692 cm$^{-1}$ | Onset at 123° C. |
| 22.8 | 1683 cm$^{-1}$ | |
| 23.4 | 1607 cm$^{-1}$ | |
| 27.3 | 1576 cm$^{-1}$ | |
| 28.0 | | |
| 29.1 | | |
| 30.6 | | |
| 33.2 | | |

Enantiomerically pure R- or S-Erdosteine Form I can be prepared by means of a process which comprises the following steps:
a) providing a solution of enantiomerically pure R- or S-Erdosteine in an organic solvent, preferably acetone;
b) adding gaseous or aqueous ammonia to precipitate enantiomerically pure R- or S-Erdosteine ammonium salt;
c) recovering the ammonium salt;
d) dissolving the ammonium salt in water;
e) acidifying the resulting water solution with hydrochloric acid;
f) cooling the acidified water solution so as to precipitate enantiomerically pure R- or S-Erdosteine Form I;
g) recovering enantiomerically pure R- or S-Erdosteine Form I.

According to a preferred embodiment of the invention, the process is conducted at a temperature between 0 and 50° C., more preferably at room temperature and enantiomerically pure Erdosteine Form I is recovered in step f) by cooling the solution to a temperature of about 0 to 10° C.

In a second embodiment, the invention provides a crystalline form of substantially enantiomerically pure R- or S-Erdosteine, referred to as Form characterized by the following physical properties:
X-ray powder diffraction pattern with peaks at about 18.3, 24.7, 28.9, 31.3, 32.3, 32.7, 36.0, 36.3, 37.2±0.2 degrees two-theta, substantially as depicted in FIG. 4;
infrared absorption spectrum with peaks at about 1708, 1692, 1644, 1538 and 1189 cm-1, substantially as depicted in FIG. 5;
melting point at about 103-142° C. (onset at 126° C.), with a DSC thermogram substantially as depicted in FIG. 6.
These data are reported in Table 3.

TABLE 3

Characterization of Erdosteine Form II

| X-ray powder diffraction pattern 2theta (deg) (FIG. 4) | Infrared absorption peaks (FIG. 5) | DSC heating curve (FIG. 6) |
|---|---|---|
| 18.3 | 1708 cm$^{-1}$ | Melting peak in range 103-142° C. |
| 24.7 | 1692 cm$^{-1}$ | Onset at 126° C. |
| 28.9 | 1644 cm$^{-1}$ | |
| 31.3 | 1538 cm$^{-1}$ | |
| 32.3 | 1189 cm$^{-1}$ | |
| 32.7 | | |
| 36.0 | | |
| 36.3 | | |
| 37.2 | | |

In another aspect, the present invention provides a process for preparing crystalline enantiomerically pure R- or S-Erdosteine Form II, comprising the following steps:
a) providing a solution of enantiomerically pure or enriched R- or S-Erdosteine in aqueous diluted ammonia;
b) acidifying the solution by addition of concentrated hydrochloric acid, optionally in the presence of a crystal seed of a previously prepared sample of R- or S-Erdosteine Form II;
c) cooling the solution;
d) recovering enantiomerically pure Erdosteine Form II.

Preferably, the process is conducted at a temperature between 0 and 50° C., more preferably at room temperature.

According to a preferred embodiment, enantiomerically pure Erdosteine Form II is recovered in step c) by cooling the solution to a temperature of about 0 to 10° C.

The polymorphs of the invention possess advantageous chemical-physical properties in respect of the racemic amorphous form, in particular in terms of flowability and dissolution rate. These advantages will be clearer by considering the following comparison between Form I of S-Erdosteine and the amorphous racemic form. The test for the evaluation of flowability showed that racemic Erdosteine does not flow through the funnel. Conversely, Form I has a mean flowing time of about 35 seconds, which allows to handle and transfer the powder more easily, and to avoid the use or reduce the amount of glidants in the finished pharmaceutical formulation.

This comparison is reported in Table 4.

TABLE 4

| Flowability comparison | |
|---|---|
| | Flowing time (mean value) |
| Racemic Erdosteine | ∞ |
| Erdosteine Form I | 35.6" |

A dissolution rate test was performed in order to define the Intrinsic Dissolution Rate of Erdosteine Form I and Racemic Erdosteine. Six thin 150 mg tablets of S-erdosteine Form I and six 150 mg tablets of racemic Erdosteine were prepared by compression with a 10 ton press and their dissolution profile in 0.1M hydrochloric acid was evaluated.

The two profiles are reported in FIG. 10, superimposed on the same graph. As can be clearly seen, the dissolution profile of Form I is very different from that of racemic, non-polymorphic Erdosteine. In fact, after 15 minutes more than 80% Form I is dissolved, while more that 25 minutes are necessary to dissolve 40% racemic Erdosteine. The higher solubility of Form I allows to obtain an improved pharmaceutical form in terms of dosage and bioavailability.

The invention is now illustrated in greater detail in the examples below.

EXAMPLES

Example 1

Preparation of S-Erdosteine Form I

Figure 1:
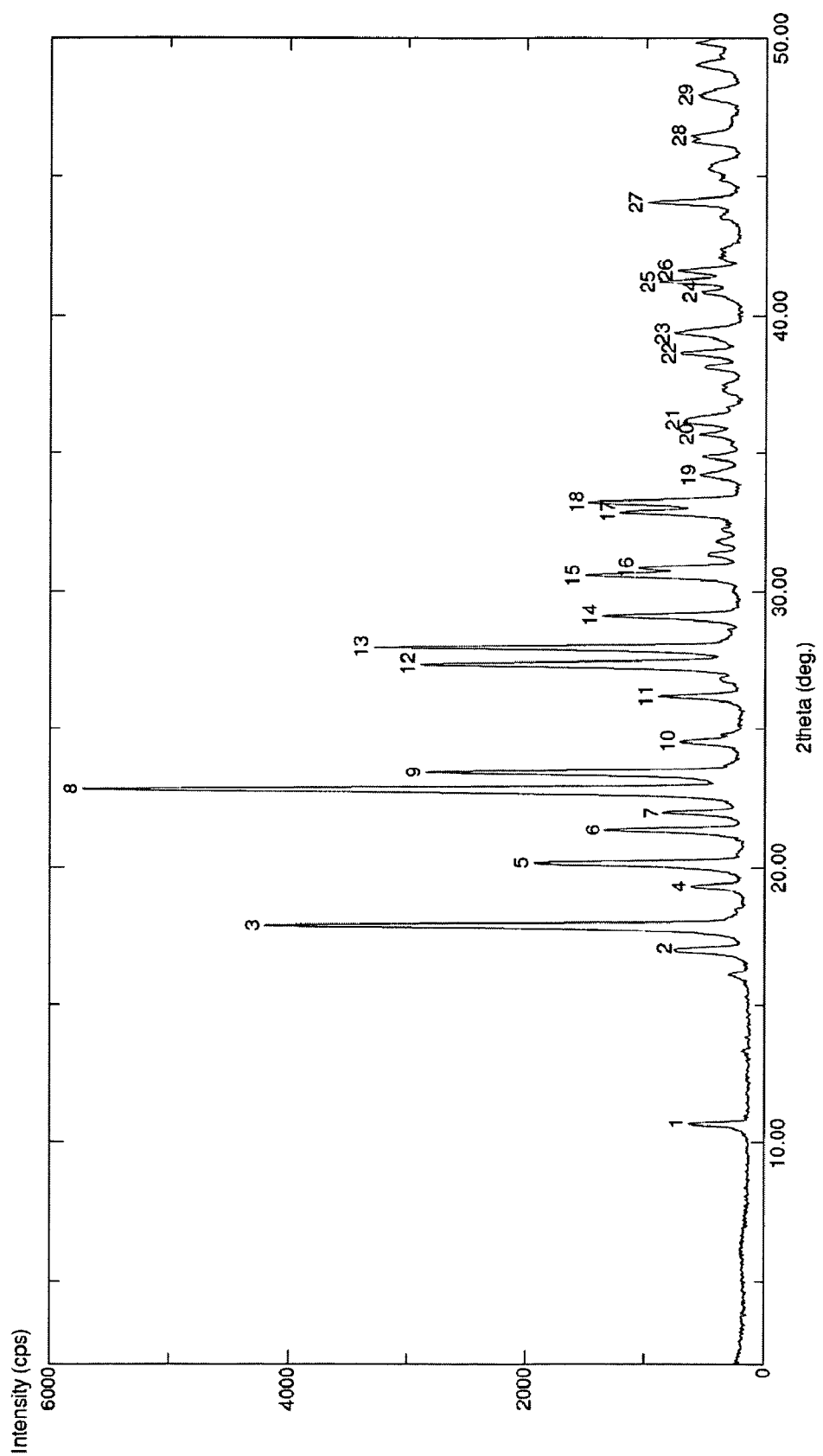
FIG. 1 is a characteristic X-ray powder diffraction spectrum of S-Erdosteine and R-Erdosteine Form I.
Figure 2:
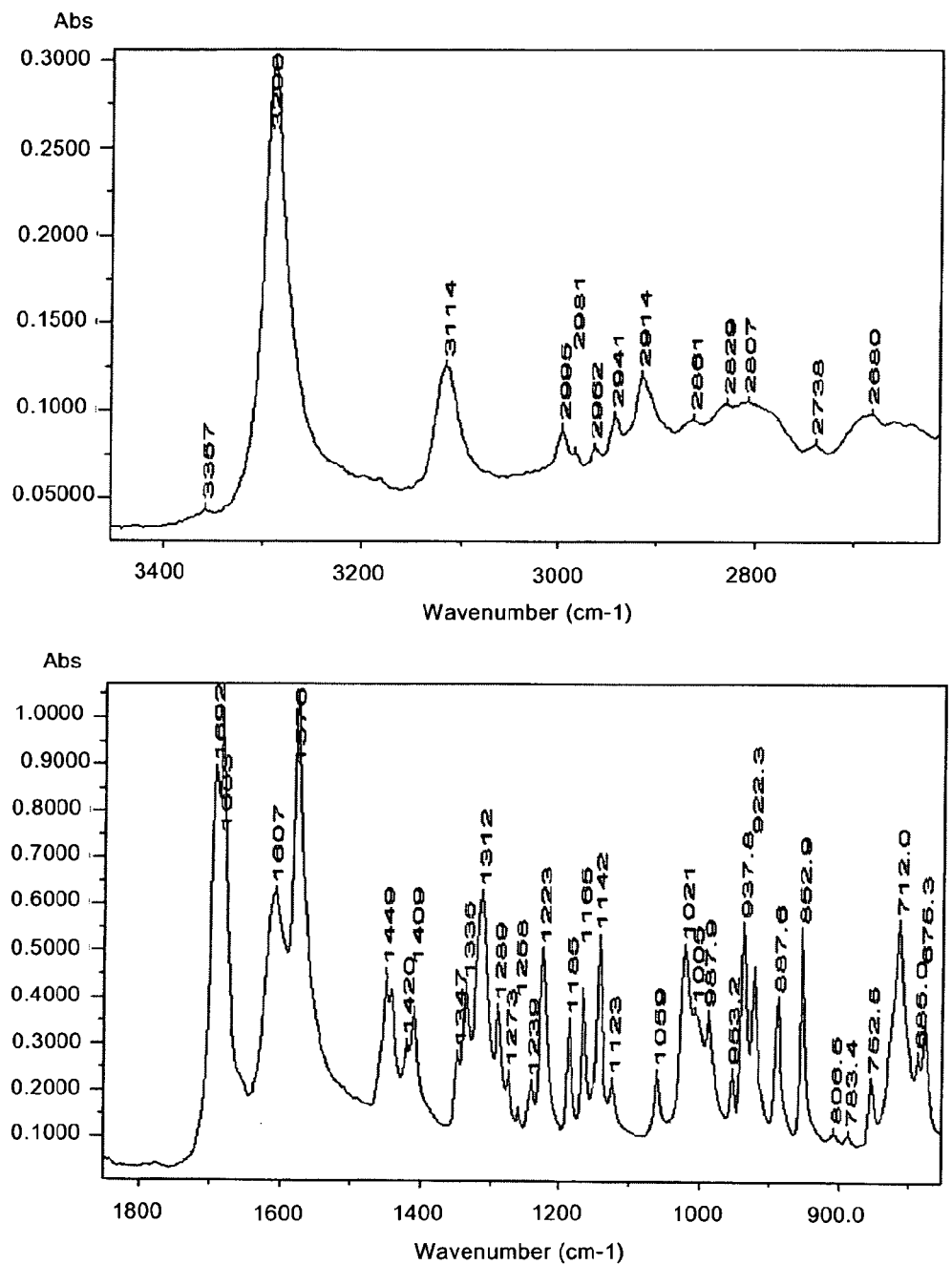
FIG. 2 is a characteristic infrared (IR) absorption spectrum of S-Erdosteine and R-Erdosteine Form I.
Figure 3:
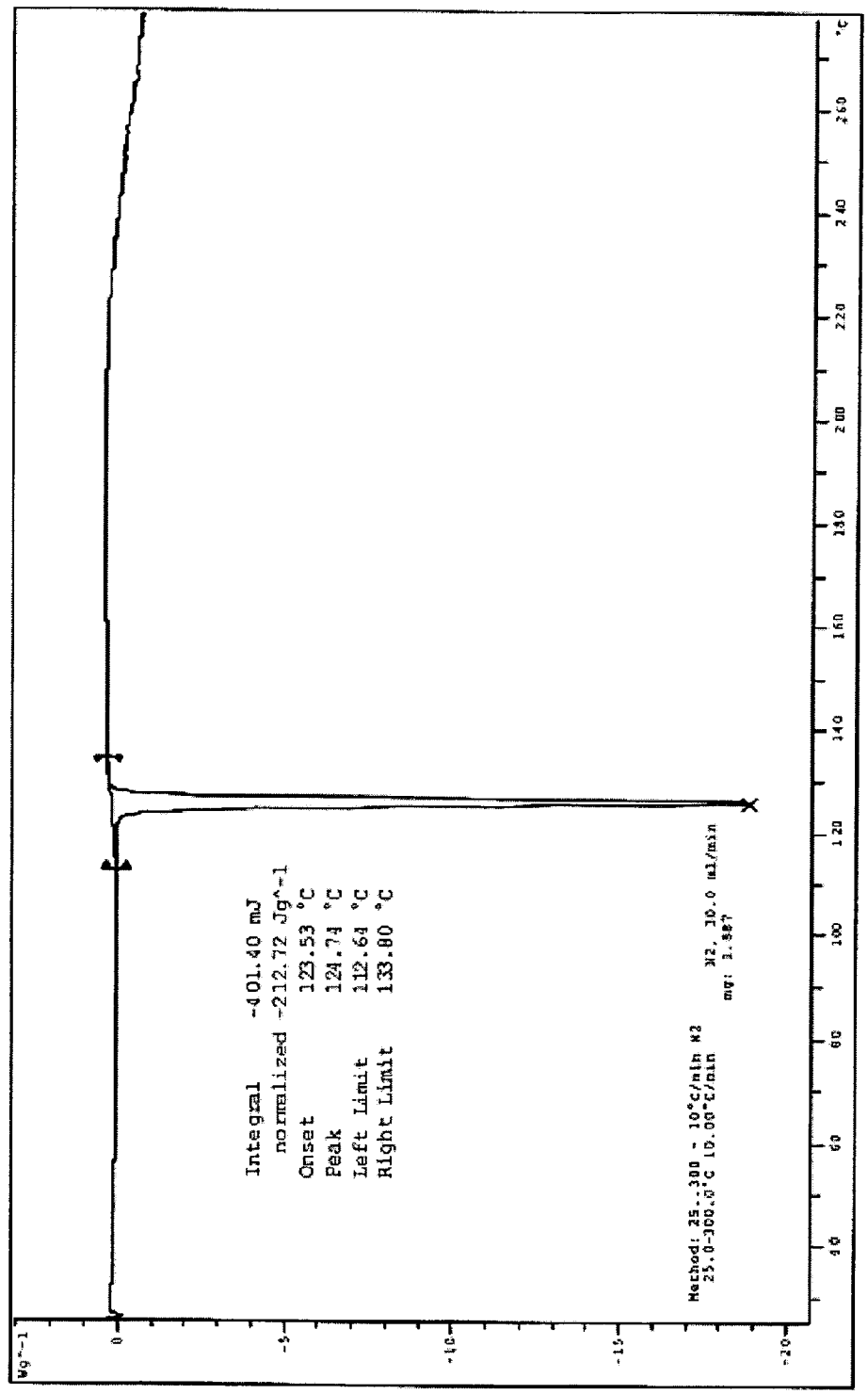
FIG. 3 is a characteristic DSC thermogram of S-Erdosteine and R-Erdosteine Form I.
Figure 4:
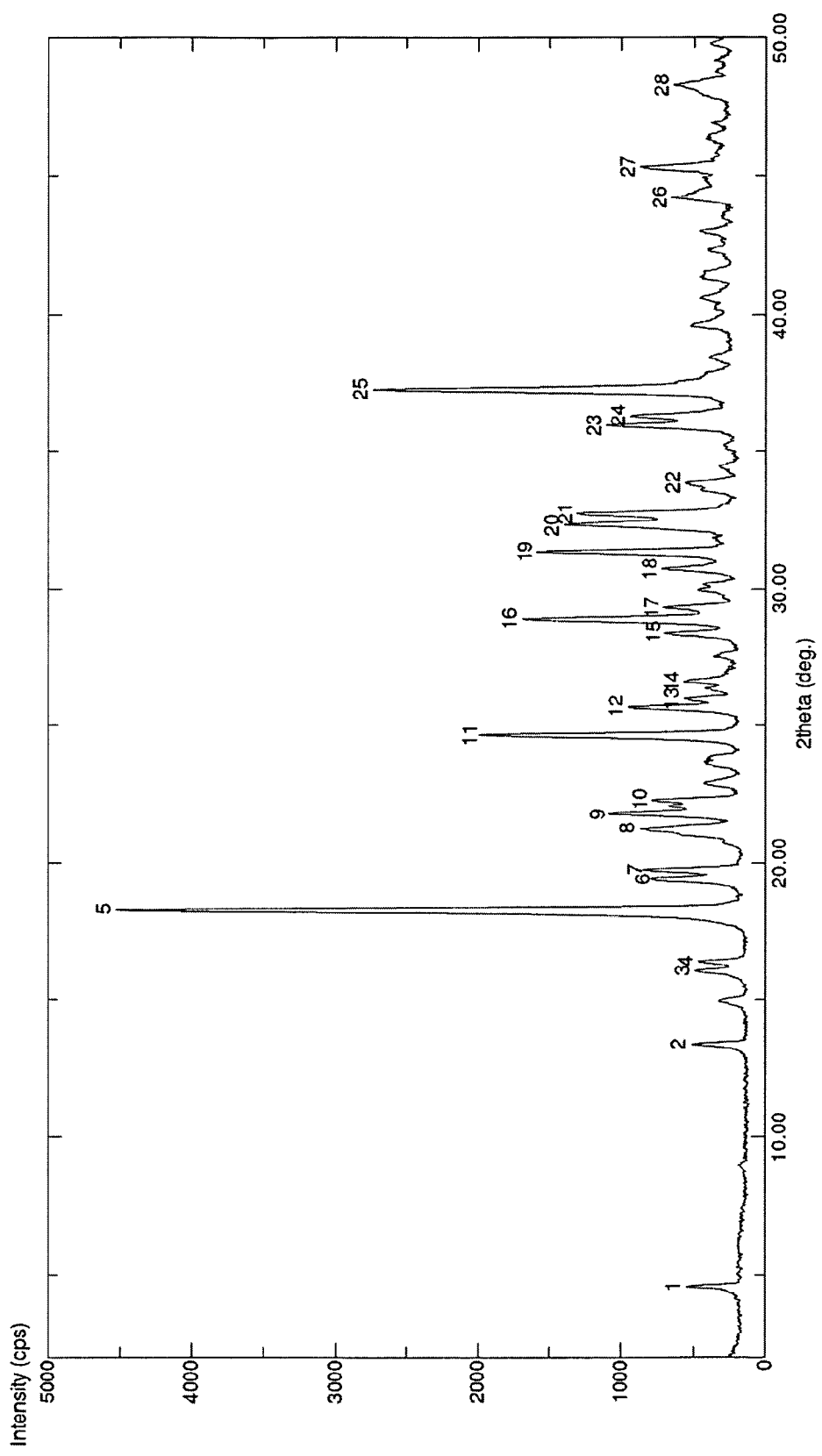
FIG. 4 is a characteristic X-ray powder diffraction spectrum of S-Erdosteine and R-Erdosteine Form II.
Figure 5:
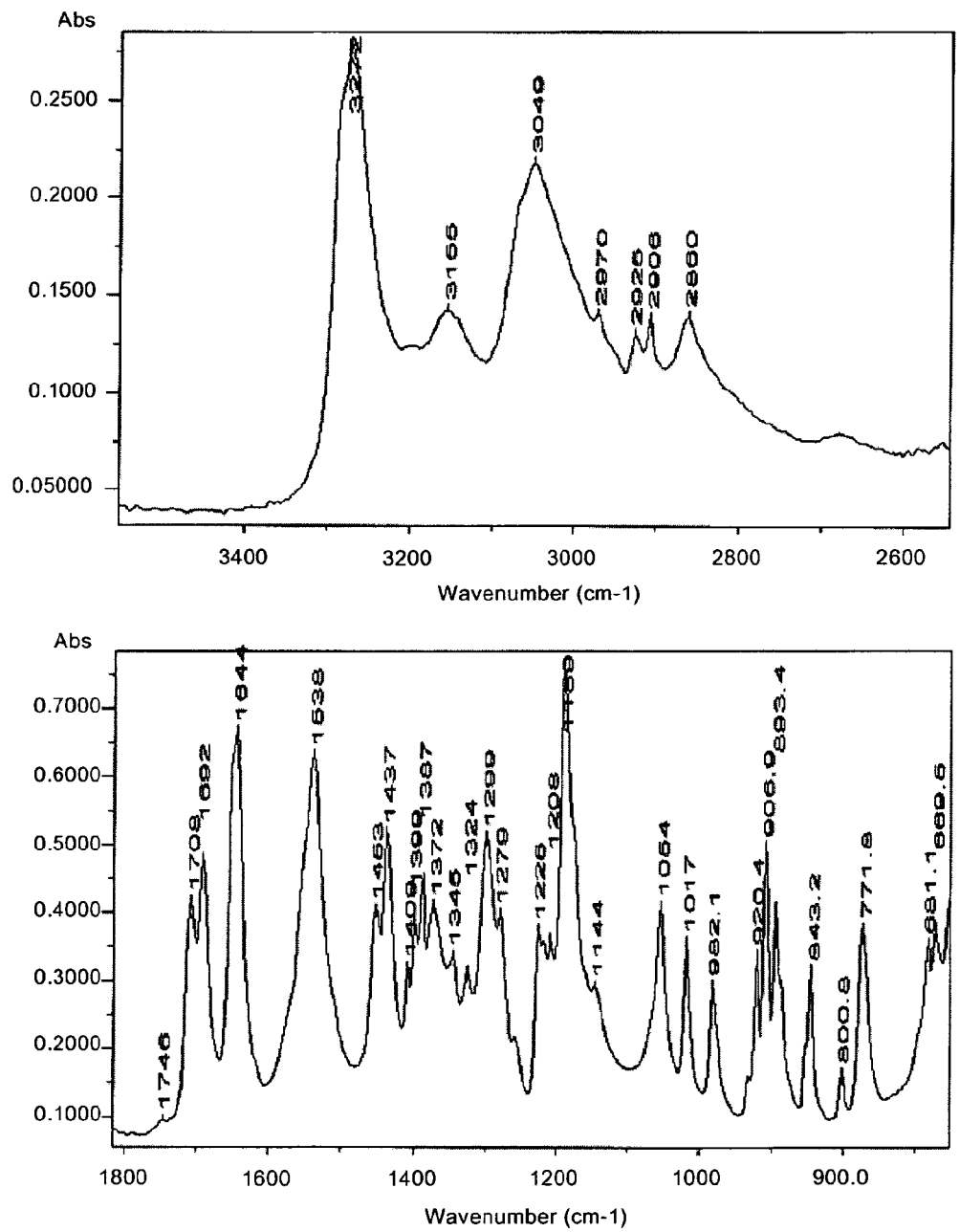
FIG. 5 is a characteristic infrared (IR) absorption spectrum of S-Erdosteine and R-Erdosteine Form II.
Figure 6:
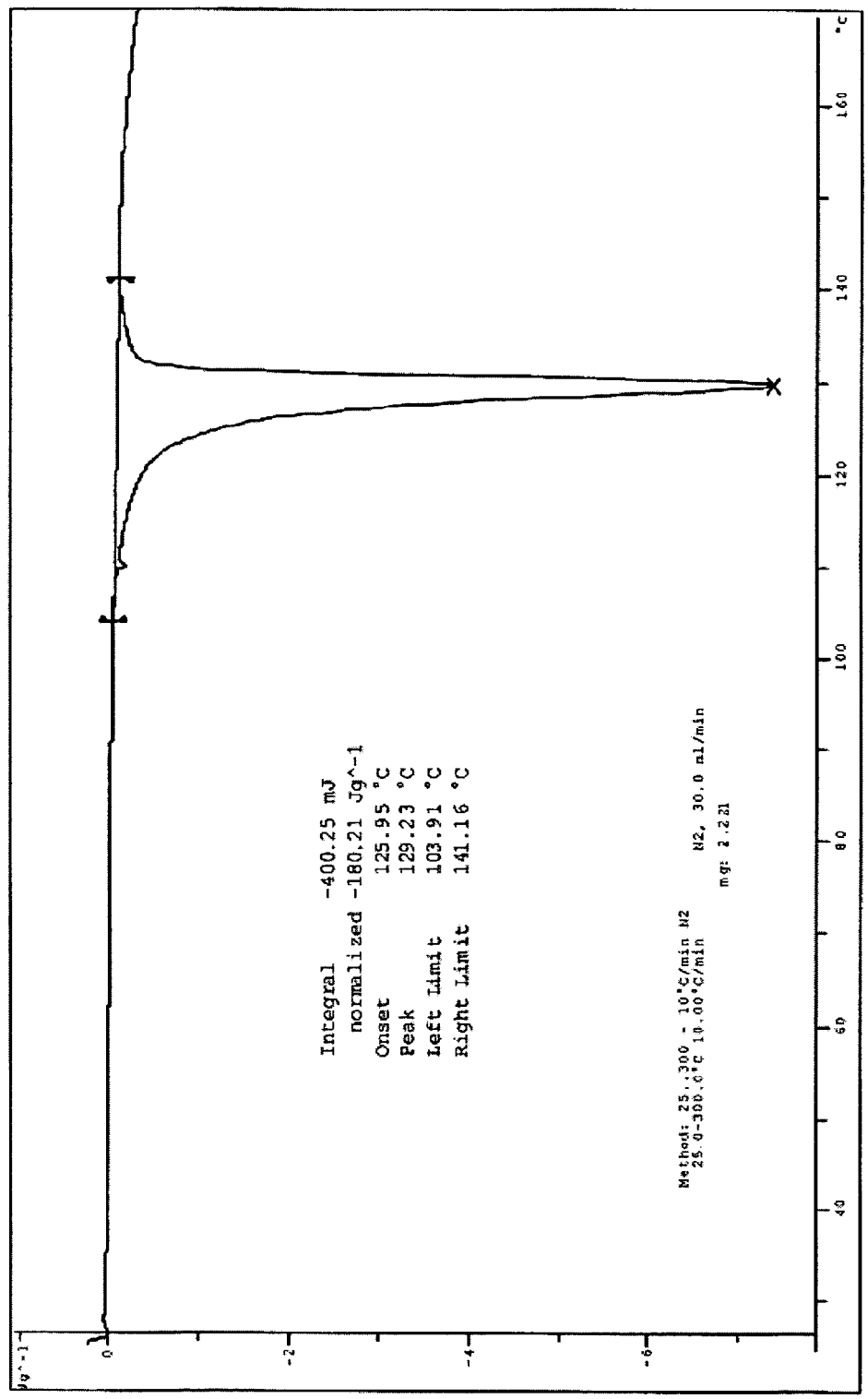
FIG. 6 is a characteristic DSC thermogram of S-Erdosteine and R-Erdosteine Form II.
Figure 7:
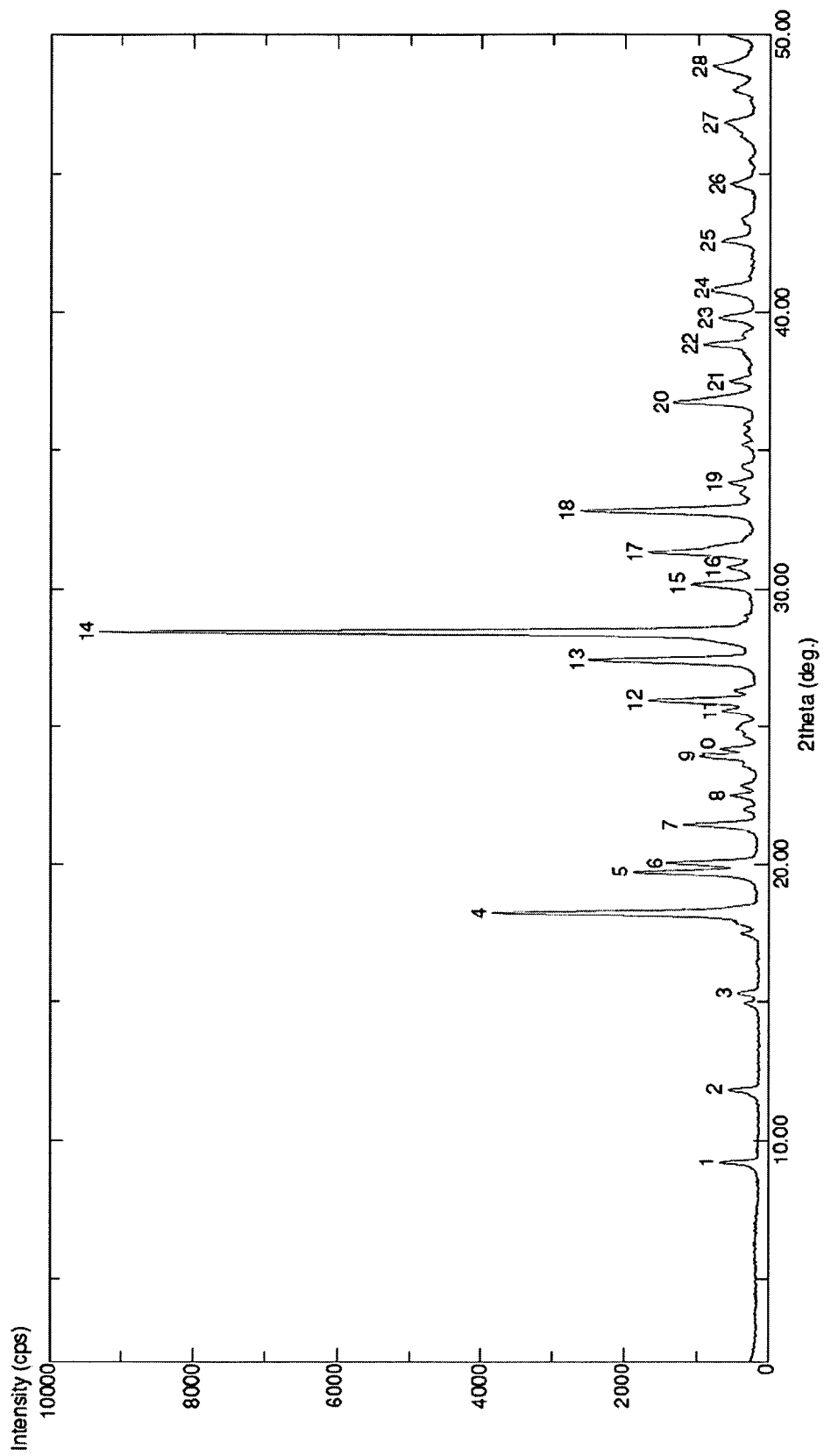
FIG. 7 is a characteristic X-ray powder diffraction spectrum of R,S-Erdosteine.
Figure 8:
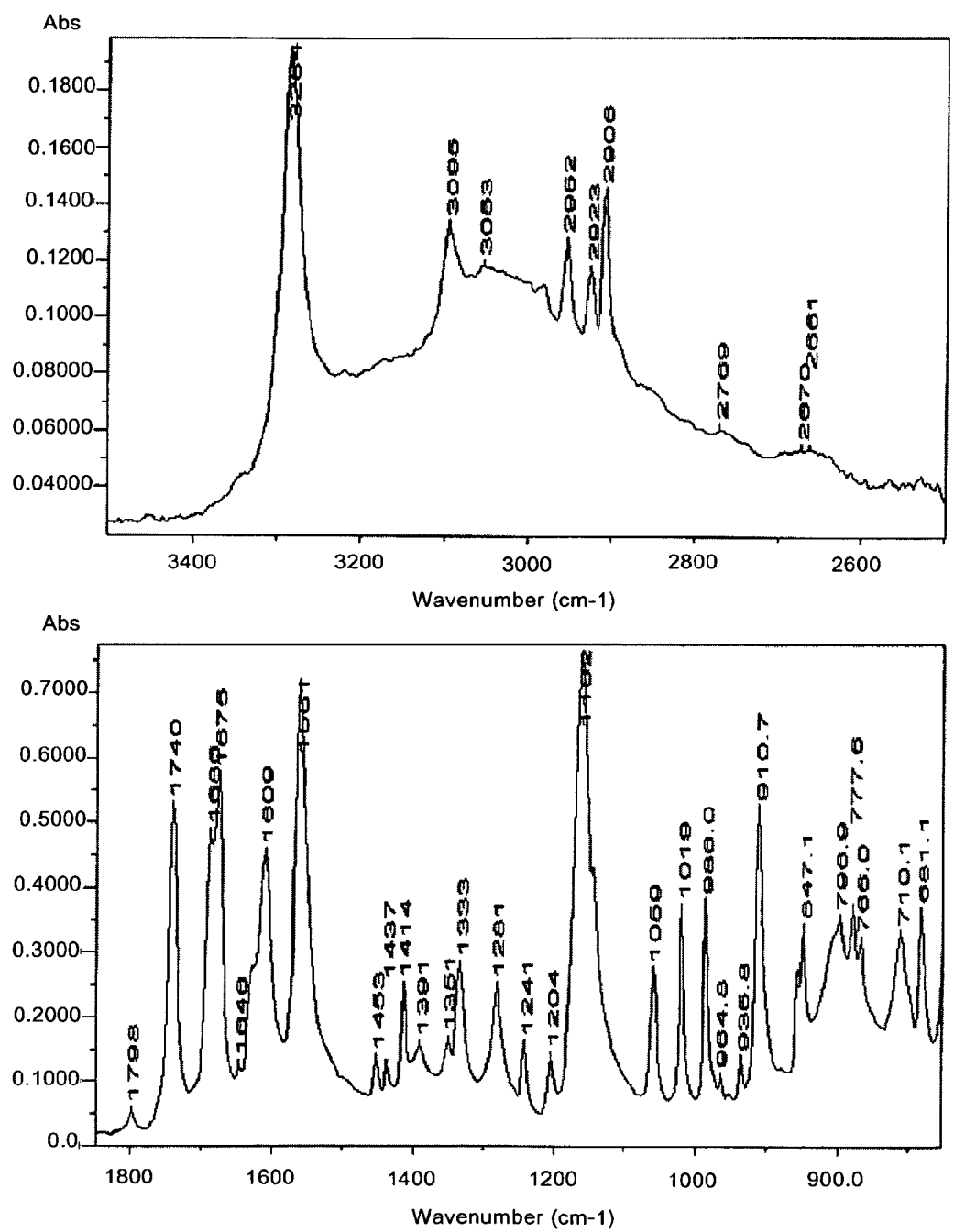
FIG. 8 is a characteristic infrared (IR) absorption spectrum of IRS-Erdosteine.
Figure 9:
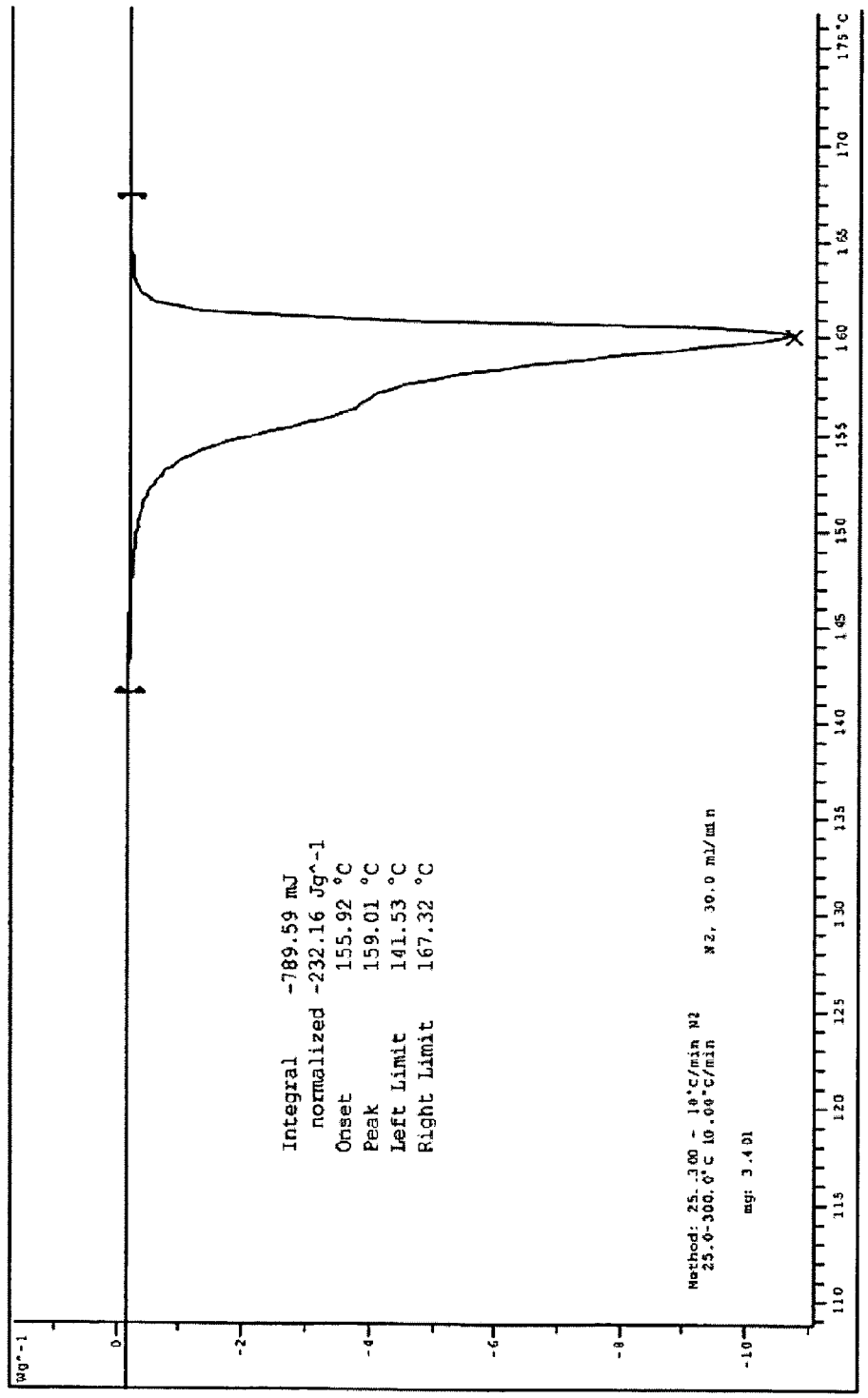
FIG. 9 is a characteristic DSC thermogram of R,S-Erdosteine.
Figure 10:
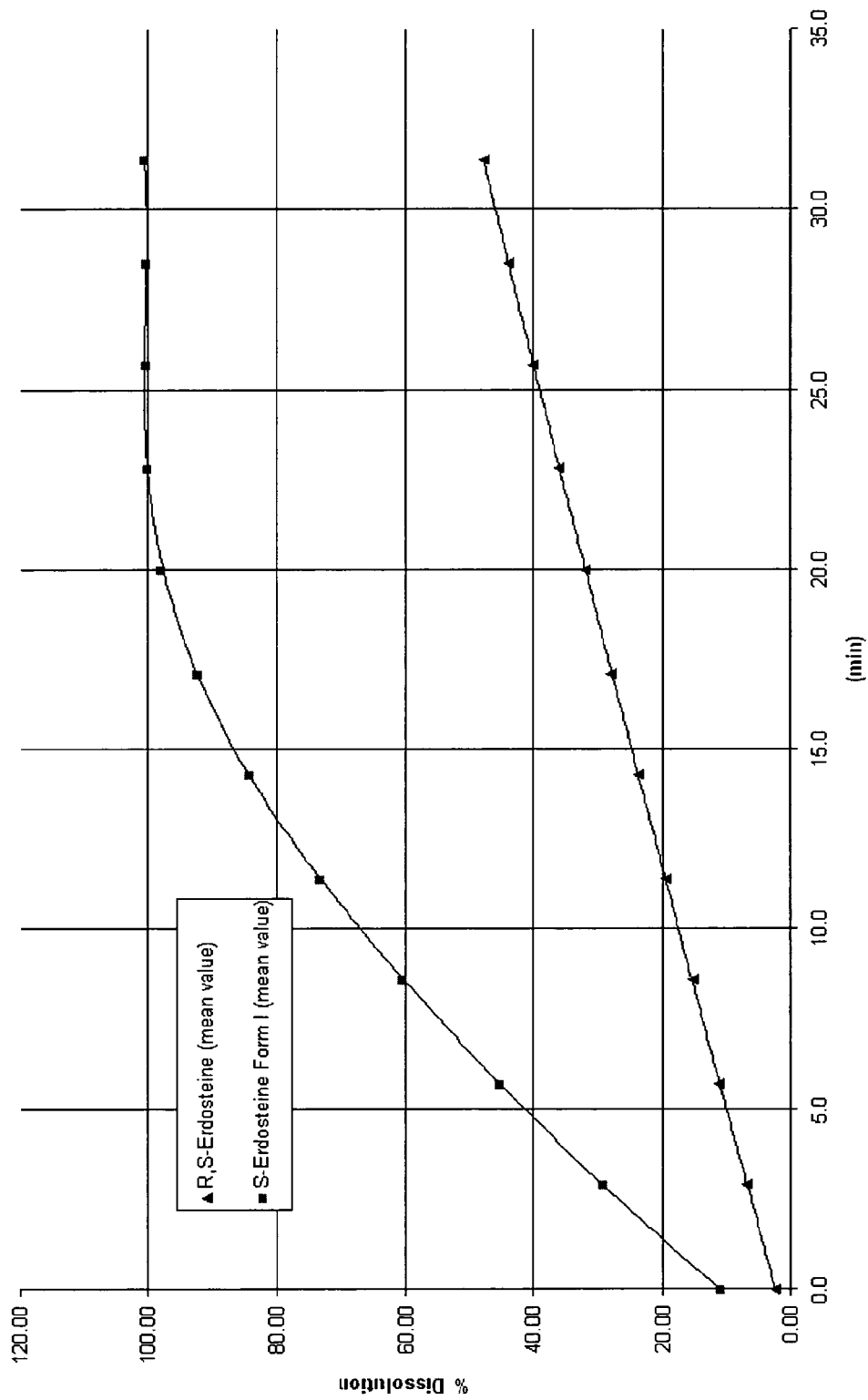
FIG. 10 is a comparison between the dissolution of S-Erdosteine Form I and Racemic Erdosteine.

Enantiomerically pure S-Erdosteine (300 g) is dissolved in acetone (5 L). 28% Aqueous ammonia (85 mL) is added, thus precipitating the ammonium salt of the desired product, which is filtered and dried under vacuum. The resulting solid is dissolved in water (1 L) and acidified to pH 3 with the addition of 37% hydrochloric acid. S-Erdosteine Form I thus obtained is filtered and dried under vacuum to obtain 250 g of pure product.

Example 2

Preparation of S-Erdosteine Form II

Enantiomerically pure S-Erdosteine (60 g) is slurried in water (60 mL) and 28% aqueous ammonia is added until pH 5.7. The clear solution is acidified to pH 3 by addition of 37% hydrochloric acid, until the pH reaches about 4. The obtained slurry is cooled at 0° C. for 6 hours and S-Erdosteine Form II thus obtained is filtered and dried under vacuum to obtain 28 g of pure product.

The invention claimed is:

1. Crystalline (R) or (S) Erdosteine Form (I), which shows:
   an X-ray powder diffraction pattern with peaks at about 17.0, 20.1, 22.8, 23.4, 27.3, 28.0, 29.1, 30.6, 33.2 ±0.2 degrees two-theta;
   an infrared absorption spectrum with peaks at about 1740, 1692, 1683, 1607 and 1576 cm-1; and
   a melting point at about 112-134° C., with onset at 123° C. and with a DSC thermogram.

2. A process for the preparation of crystalline R- or S-Erdosteine polymorph (I) as defined in claim 1, said process comprising:
   a) providing a solution of enantiomerically pure Erdosteine in an organic solvent;
   b) adding gaseous or aqueous ammonia to precipitate R- or S-Erdosteine ammonium salt;
   c) recovering the ammonium salt;
   d) dissolving the ammonium salt in water;
   e) acidifying the water solution with hydrochloric acid;
   f) cooling the acidified water solution so as to precipitate enantiomerically pure Erdosteine Form I;
   g) recovering enantiomerically pure R- or S-Erdosteine Form I.

3. The process of claim 2 wherein the organic solvent is acetone.

4. The process of claim 2 which is carried out at a temperature comprised between 0 and 50° C.

5. The process of claim 2 wherein step f) is carried out cooling the solution to 0-10° C.

6. Crystalline (R) or (S) Erdosteine Form (II), which shows:
   an X-ray powder diffraction pattern with peaks at about 18.3, 24.7, 28.9, 31.3, 32.3, 32.7, 36.0, 36.3, 37.2 ±0.2 degrees two-theta;
   an infrared absorption spectrum with peaks at about 1708, 1692, 1644, 1538 and 1189 cm-1; and
   a melting point at about 103-142° C. (onset at 126° C.), with a DSC thermogram.

7. A process for the preparation of crystalline R- or S-Erdosteine polymorph (II) as defined in claim 6, said process comprising:
   a) providing a solution of enantiomerically pure or enriched Erdosteine in aqueous diluted ammonia;
   b) acidifying the solution by addition of concentrated hydrochloric acid,;
   c) cooling the solution;
   d) recovering enantiomerically pure R- or S-Erdosteine Form II.

8. The process of claim 7 which is carried out at a temperature comprised between 0 and 50° C.

9. The process of claim 7 wherein step c) is carried out cooling the solution to 0-10° C.

10. The process of claim 7, wherein step b) is carried out in the presence of a crystal seed of a previously prepared sample of R- or S-Erdosteine Form II.

* * * * *